United States Patent [19]
Peabody et al.

[11] Patent Number: 5,643,201
[45] Date of Patent: Jul. 1, 1997

[54] CONTINUOUS PERITONEAL DIALYSIS APPARATUS

[76] Inventors: Alan M. Peabody, 5-B Sugar Creek Villas, Greer, S.C. 29650; James T. Boag, 3405 E. John St., Seattle, Wash. 98112; Ted M. Walters, 303 Brighton Rd., Anderson, S.C. 29621

[21] Appl. No.: 328,664

[22] Filed: Oct. 25, 1994

Related U.S. Application Data

[63] Continuation of Ser. No. 653,078, Feb. 8, 1991, abandoned, which is a continuation-in-part of Ser. No. 200,624, May 31, 1988, Pat. No. 5,004,459, which is a continuation-in-part of Ser. No. 858,645, May 2, 1986, Pat. No. 4,747,822, which is a continuation-in-part of Ser. No. 840,142, Mar. 17, 1986, Pat. No. 4,718,890, which is a continuation-in-part of Ser. No. 629,130, Jul. 9, 1984, Pat. No. 4,586,920.

[51] Int. Cl.$^6$ ................................................ A61M 1/00
[52] U.S. Cl. ................................ 604/31; 604/29; 604/65
[58] Field of Search ........................... 604/27–31, 65, 604/67; 128/DIG. 12, DIG. 13

[56] References Cited

U.S. PATENT DOCUMENTS

| | | | |
|---|---|---|---|
| 4,190,047 | 2/1980 | Jacobsen et al. | 128/213 |
| 4,618,343 | 10/1986 | Polaschegg | 604/29 |

FOREIGN PATENT DOCUMENTS

| | | | |
|---|---|---|---|
| 1173712 | 9/1984 | Canada | 604/28 |

*Primary Examiner*—Corrine M. McDermott
*Attorney, Agent, or Firm*—Cort Flint

[57] ABSTRACT

A peritoneal dialysis system is illustrated of the continuous flow type which includes a reverse osmosis unit which prepares sterilized and filtered water for mixing with a sterilized dialysate in a dialysis production unit. The process includes proportioning water, dialysis concentrate, and dextrose to provide a dialysis fluid which is then heated and sterilized. The fluid may be accumulated in a reservoir which accumulates a desired amount of dialysis fluid as measured by a load cell which measures the weight of the fluid. The dialysis process may be used with a single or double catheter. A desired amount of fluid is delivered to the peritoneal cavity as measured by the load cell, and a desired amount of fluid is drained from the cavity as measured by a load cell into a drain reservoir so that a desired amount of peritoneal dialysis fluid is maintained in the cavity during dialysis. Alternately, or in addition, flowmeters are utilized to measure the flow rate of the fluid in and out of the peritoneal cavity, either simultaneously or cyclic, and control the amount of fluid in the cavity. Preferably, the process and system includes a double flow catheter in which the flow of dialysis fluid through the inflow passage and the outflow passage of the double flow catheter are simultaneous. During this time, the volume of fluid in the peritoneal cavity is monitored by an ultrasonic or other suitable sensor so that over extension of the cavity does not occur. In a preferred tidal dialysis regime, either the load cell and/or the flowmeter arrangement is utilized to fill the cavity with dialysis fluid, drain the cavity to a reserve volume, and refill the cavity with a tidal volume to provide a dialysis regime which includes a desired number of fill and partial drain cycles wherein a puddle of dialysis fluid always remains in the cavity.

28 Claims, 4 Drawing Sheets

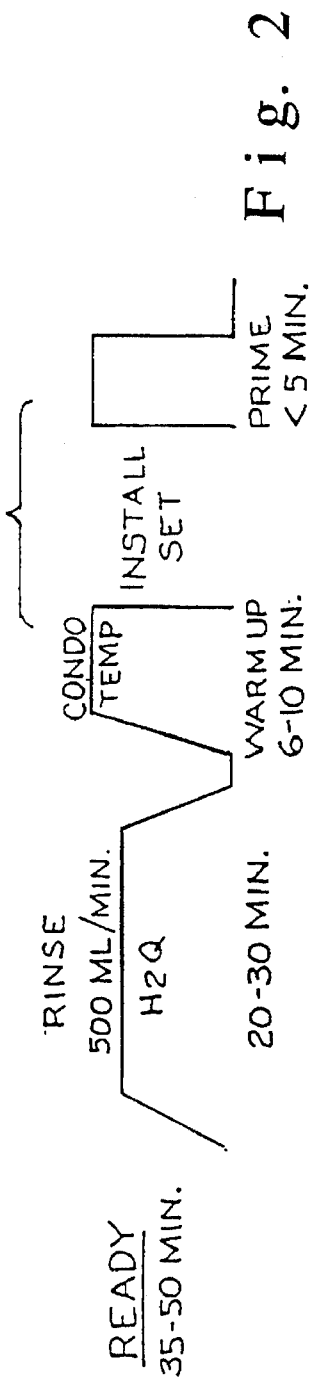
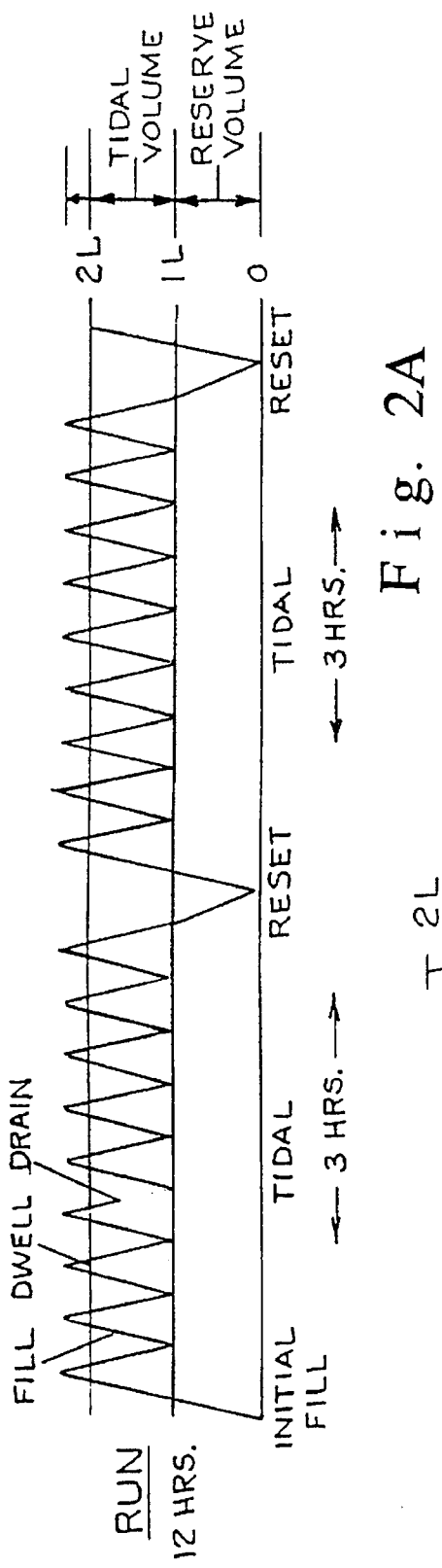

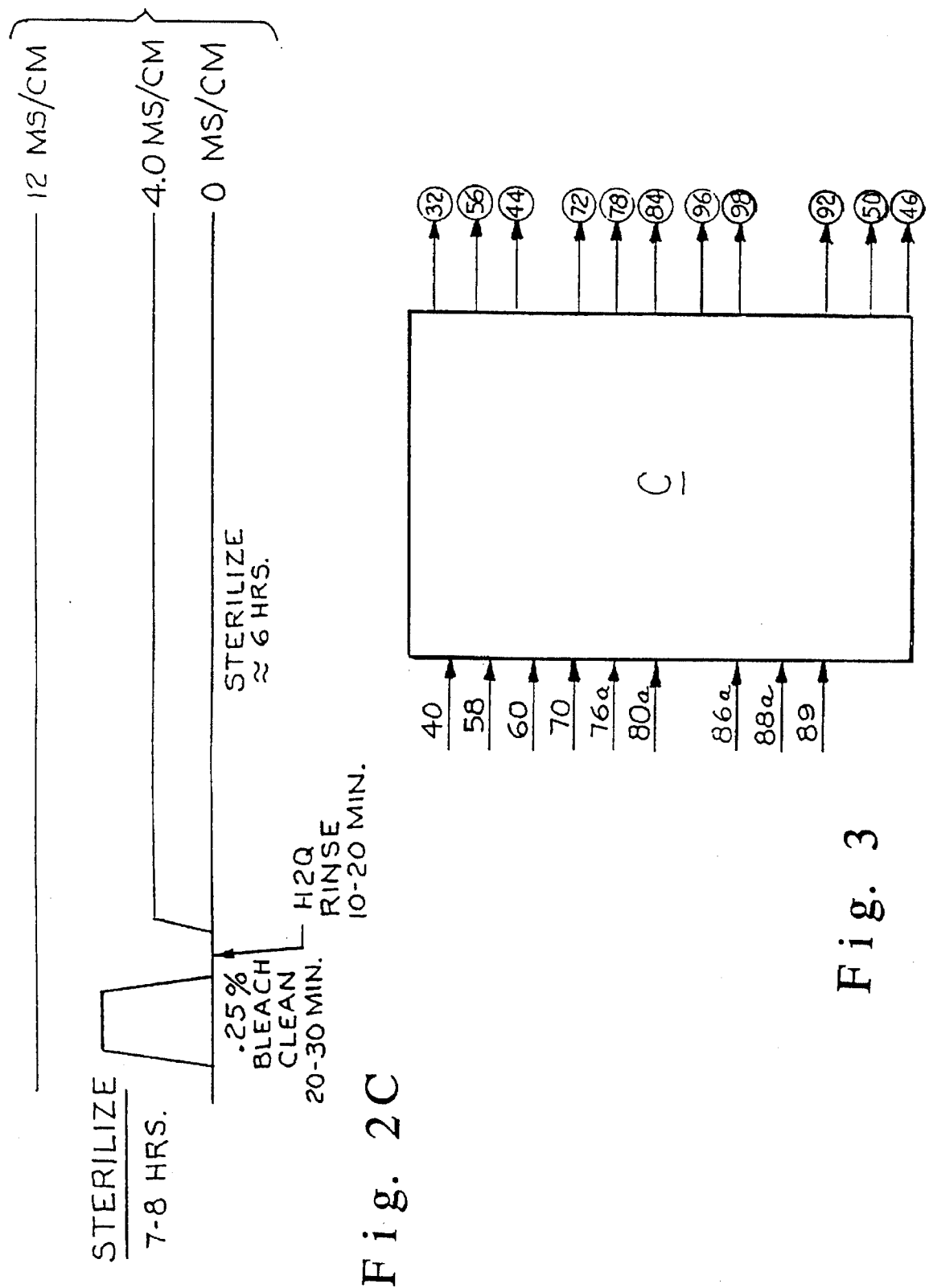

CONTINUOUS PERITONEAL DIALYSIS APPARATUS

CROSS REFERENCE TO RELATED APPLICATIONS

This is a continuation of application Ser. No. 07/653,078 filed Feb. 8, 1991, now abandoned, which is a continuation-in-part of Ser. No. 07/200,624 filed May 31, 1988, now U.S. Pat. No. 5,004,459, which is a continuation-in-part of Ser. No. 06/858,645 filed May 2, 1986, now U.S. Pat. No. 4,747,822, which is a continuation-in-part of Ser. No. 06/840,142 filed Mar. 17, 1986, (now U.S. Pat. No. 4,718,890) which is a continuation-in-part of Ser. No. 06/629,130 filed Jul. 9, 1984, now U.S. Pat. No. 4,586,920.

BACKGROUND OF THE INVENTION

The invention relates to a dialysis process for purifying the blood by exchange across the peritoneal membrane during a continuous peritoneal process.

Heretofore, artificial kidney users have relied basically on two processes for purifying the blood. Hemodialysis involves the circulation of blood through a dialysis machine in which an exchange of toxic metabolites takes place across an artificial membrane outside the patient's body. This process requires the assistance of trained personnel and subjects the patient to dangers of mechanical malfunction, and rapid shifts of fluid and metabolites, and surgery involving blood vessels, is involved.

Peritoneal dialysis involves the installation of a sterile dialysate into the peritoneal cavity. The dialysate is discarded after absorbing waste metabolites. The process is repeated until the blood level of metabolites is reduced to a desired level. This method is commonly referred to as the "Batch" method due to the fact that numerous one or two liter bottles or bags of fresh dialysate solution are utilized, requiring multiple connections to be made to the catheter inserted in the peritoneal cavity. The multiple connections made during the course of the dialysis have been thought to be a major cause of the high instance of peritonitis.

Chronic ambulatory peritoneal dialysis offers peritoneal dialysis while still allowing the patient freedom of movement. However, the chronic ambulatory peritoneal dialysis must be done in absence of a machine. Multiple bottles or bags of dialysis must be infused daily. The bag of dialysate is worn by the patient. The multiple installations per day require that multiple connections of bags or bottles to the peritoneal catheter be made. The production of bulk sterile dialysis for the peritoneal process has not been shown to be practical for large scale application particularly for home dialysis.

U.S. Pat. No. 4,311,587 seeks to avoid some of the above problems with peritoneal dialysis by providing a sub-micron filter on line with the fresh dialysate to prevent peritoneal contamination. The system is perambulatory and the bag of dialysate is worn by the patient. The bag may be pressurized by numerous methods and is connected only to the inflow side of the filter. The outflow port of the filter is connected on the other side of the filter so that no peritoneal contaminating source is connected directly to the peritoneal cavity. The system is still basically a batch type system in that multiple bottles or bags of dialysate must be connected to the filter even though direct connection to the peritoneal catheter is not required.

U.S. Patent No. 4,338,190 discloses a system and process which attempts to avoid the batch process method utilized heretofore in peritoneal dialysis wherein a closed loop peritoneal circuit is provided having a selective membrane across which toxic metabolites are exchanged. A solution is passed on the other side of the selective membrane to maintain the original concentration of sugar and salt in the peritoneal fluid as the toxic metabolites pass the separator membrane. A concentrate of sugar and salts is mixed at a desired ratio with water to make up the dialysis fluid. The conductivity of the fluid may be automatically monitored to adjust the concentration of the fluid during its recirculation. A double peritoneal catheter provides for the inflow and outflow of the peritoneal fluid. The peritoneal fluid is constantly recirculated through the peritoneal cavity. The efficiency of the dialysis becomes reduced slightly because of residual toxins which are put back into the peritoneal cavity. The selective membrane is an expensive disposable item which means that the cost of operating the system is high unless the membrane is recleaned. Pumping the peritoneal fluid through the peritoneal cavity is required making it difficult to assure that the patient stays properly distended during the dialysis process. If the peritoneal membrane is not fully distended, it becomes convoluted around the intestines and pockets are formed where the peritoneal fluid can sequester. Incomplete circulation results in decreased efficiency of dialysis. No control is maintained over the level of peritoneal fluid in the peritoneal circuit. There is no way of replenishing the peritoneal fluid should the circuit run low on fluid or run dry.

U.S. Pat. No. 3,545,438 discloses a peritoneal dialysis method which provides for partially reusing a portion of the dialysis fluid. The spent fluid becomes mixed with fresh dialysate. There is no control or monitoring of the fluid in and out as would allow the dialysate to flow in the peritoneal cavity in a continuous manner.

U.S. Patent No. 3,707,967, corresponding to German Patent No. 2,149,040, apparently discloses a closed loop dialysis system wherein the dialysis fluid is continuously circulated through the peritoneal membrane, generally without flow control and monitoring of inflow and outflow lines in a continuous manner.

U.S. Pat. No. 3,709,222 discloses a peritoneal dialysis method generally of the batch type. The amount of dialysis fluid entering the peritoneal cavity and the pressure of the peritoneal cavity are controlled by varying the height of a pressure relief chamber. This can be both inaccurate and unreliable, and requires that an attendant be present in order to carry out the process. The cycles involved in the process are rather complicated involving an initial priming cycle which involves the filling of a proportion chamber, the pressure relief chamber and a return chamber. To begin the process, dialysis fluid is allowed to enter the peritoneal cavity from the pressure relief chamber until the chamber is moved to a lower position which prevents the fluid from flowing. Next, an automatic cycling begins in which the fluid is pumped out of the cavity into the return chamber. Next, an inflow cycle begins in which the fluid is pumped from the return chamber to the proportional chamber which forces fresh dialysis from the proportioning chamber into the pressure relief chamber from where it flows into the patient. Next, there is an equilibrium cycle in which dialysis fluid is drained from the proportioning chamber and fresh dialysis fluid is added. Apparently, during this time, dialysis fluid remains in the cavity. The process then switches back to the outflow cycle in which fluid is pumped from the cavity to the return chamber.

French Patent No. 2,371,931 discloses a peritoneal process having a single line used for inflow and outflow. The method includes pumping in a certain amount of dialysate, letting it equilibrate for a prescribed dwell time, and removing the dialysate. This is, in essence, an automatic "batch" system.

U.S. Pat. No. 4,412,917 discloses a peritoneal dialysis system wherein a prescribed volume of fluid is pumped into the peritoneal cavity and drained. The installation of fluid to the patient can be controlled by counting pump revolutions or pumping time and by monitoring the total weight of the reservoirs which contain the source and drain fluids to achieve a desired amount of fluid received by the patient. After the fluid is drained, the patient's fluid balance is determined by weighing the increase and total weight of fluid on output scales to indicate the extra amount of fluid (ultrafiltrate) received from a patient. The fill and drain cycles may be repeated until either a desired amount of fluid is used or the change in fluid balance reported by the scales is of a desired magnitude.

It is also known in peritoneal dialysis to use a reverse osmosis unit to supply water which is passed through a heat exchanger for heating. The water is subsequently mixed with a dialysis concentrate, and optionally, dextrose, which are mixed in a predetermined ratio to provide a dialysate. The dialysate may be gravity fed or pumped to the patient, and thereafter drained either by gravity or pumping in a semi-automatic manner. However, the system is complex for the patient to operate, and has difficulty in meeting safety requirements. It is also known to mix dextrose with the water and dialysis concentrate to effect the osmolality over pressure sensors are utilized to sense an excessive pressure condition in the peritoneal cavity.

Tidal peritoneal dialysis is a technique where, after an initial fill of the peritoneal cavity, less than 50% of dialysate is drained and replaced by fresh dialysis fluid with each cycle, leaving the majority of the dialysate in constant contact with the peritoneal membrane until the end of the dialysis session when the fluid is drained as completely as possible. The factors determining the efficiency of dialysis with the tidal technique include the minimum volume of fluid in the peritoneal cavity assuring constant and full contact between the peritoneal membrane and dialysate, that is the reserve volume, and proper mixing of fluid in the peritoneal cavity by a sufficiently high tidal exchange volume. While the technique of tidal peritoneal dialysis is sound and efficient, there is a lack of suitable systems for implementing the tidal technique of peritoneal dialysis in a practical manner. None of the prior peritoneal dialysis methods and systems described previously are entirely suitable.

Accordingly, an important object of the present invention is to provide a continuous peritoneal dialysis system and method which avoid the inherent problems and dangers of a batch type peritoneal dialysis system.

Still another important object of the present invention is to provide a peritoneal dialysis system having a high rate of dialysate exchange providing increased dialysis efficiency.

Still another important object of the present invention is to provide a peritoneal dialysis system and method having a high rate of dialysate exchange and dialysis efficiency in which the osmolality of the fluid is continuously adjusted in response to the amount of fluid removed from the patient.

Still another important object of the present invention is to provide a continuous peritoneal dialysis system and method which may be used to carry out a continuous peritoneal dialysis using tidal dialysis techniques in the patient's peritoneal membrane.

Yet another important object of the present invention is to provide a continuous flow peritoneal dialysis system and method in which the pressure and volume of dialysate in the patient's peritoneal membrane may be monitored without the need of a medical attendant.

SUMMARY OF THE INVENTION

The above objectives are accomplished according to the present invention by a system for performing a continuous peritoneal dialysis process which comprises a virtually unlimited supply of sterilized dialysis fluid, and an inflow delivery value for filling the peritoneal cavity with dialysis fluid through a catheter from the supply source. An outflow delivery value controls draining the dialysis fluid from the peritoneal cavity. An inflow measuring meter monitors a function of an inflow of dialysis fluid which fills the peritoneal cavity through the inflow catheter and generates an inflow signal representing the amount of fluid delivered into the peritoneal cavity. An outflow measuring meter monitors a function of an outflow of dialysis fluid drained through the outflow catheter and generates an outflow signal representing the amount of fluid drained from the peritoneal cavity.

A control computer controls the inflow delivery value to control the amount of dialysis fluid delivered to the peritoneal cavity in response to the inflow signal, and controls the outflow delivery value to control the amount of dialysis fluid drained from the peritoneal cavity in response to the outflow signal.

Sterilized dialysis fluid may be accumulated in a first reservoir. A first weighing cell weighs the dialysis fluid in the first reservoir to accumulate a first prescribed volume of dialysis fluid in said the first reservoir and generates a first weight signal. The inflow delivery value delivers the dialysis fluid from the first reservoir to the peritoneal cavity of a patient. The outflow delivery means for draining dialysis fluid from the peritoneal cavity of the patient into a second reservoir. A second weighing cell weighs the dialysis fluid in the second reservoir to determine a second prescribed volume of dialysis fluid and generates a second weight signal. The control computer may also control the inflow delivery value to terminate filling of the peritoneal cavity in response to the first weight signal and inflow signal, and control the outflow delivery value to terminate the draining of the dialysis fluid from the peritoneal cavity in response to the second weight signal and the outflow signal.

There is a monitor for monitoring a function of the fluid volume in the peritoneal cavity for controlling the outflow delivery value to adjust the amount of dialysis fluid in the peritoneal cavity to maintain a desired fluid volume in the peritoneal cavity. The monitor may be an ultrasonic sensing or a resistive sensing device.

The control computer may control the inflow and the outflow delivery values for filling and draining the dialysis fluid so as to maintain a desired reserve volume of dialysis fluid in the peritoneal cavity which is effective for dialysis. The inflow and outflow delivery values may be controlled to initially fill the peritoneal cavity with the first prescribed volume of dialysis fluid, drain the dialysis fluid from the peritoneal cavity to leave a reserve volume of dialysis fluid remaining in the cavity which is less than the first prescribed volume, and fill the peritoneal cavity with a tidal volume of dialysis fluid. The control computer then repeats draining of the peritoneal cavity to the reserve volume and filling of the peritoneal cavity with the tidal volume for a prescribed number (N) of cycles of total volume. The control computer controls the inflow and outflow delivery values for totally draining the dialysis fluid from the peritoneal cavity at the end of N cycles. The control then repeats an initial filling of the peritoneal cavity with dialysis fluid, and drains the peritoneal cavity to the reserve volume and fills the peritoneal cavity with the tidal volume again for a prescribed number (N) of cycles, or total exchange volume.

A heater heats the dialysis fluid prior to accumulating the first volume of dialysis fluid in the first reservoir to sterilize the dialysis fluid. A storage stores the dialysis fluid at a prescribed temperature and for a prescribed length of time prior to delivering the dialysis fluid to the first reservoir to kill the bacteria in the dialysis fluid. A deaerator deaerates the dialysis fluid prior to accumulating the dialysis fluid in the first reservoir. A detector detects the conductivity of the dialysis fluid prior to delivering the dialysis fluid to the first reservoir for maintaining a prescribed conductivity. A sensor senses the amount of water removed from the patient during dialysis and adjusts an amount of glucose in the dialysis fluid to adjust the osmolality and maintain a prescribed weight removal from the patient.

In accordance with the invention, a method for continuous peritoneal dialysis includes accumulating a sterilized dialysis fluid in a first reservoir, weighing the dialysis fluid in the first reservoir to determine a first prescribed volume of dialysis fluid, and filling a peritoneal cavity of a patient with the first prescribed volume of dialysis fluid from the first reservoir. Next, the method includes draining the dialysis fluid from the peritoneal cavity of the patient into a second reservoir, weighing the dialysis fluid in the second reservoir to determine a second prescribed volume of dialysis fluid, and terminating the draining of the dialysis fluid from the peritoneal cavity in response to weighing of the second prescribed volume of dialysis fluid in the second reservoir. The volume of fluid in the peritoneal cavity of the patient is monitored and the amount of dialysis fluid in the peritoneal cavity is adjusted to provide a desired volume in the peritoneal cavity. The flow of the dialysis fluid may also be monitored during the filling to control the amount of dialysis fluid which fills the peritoneal cavity. The flow of the dialysis fluid during draining may also be monitored to control the amount of fluid which is drained from the peritoneal cavity. A tidal method includes initially filling the peritoneal cavity with the first prescribed volume of dialysis fluid, draining the dialysis fluid from the peritoneal cavity to leave a reserve volume of dialysis fluid remaining in the cavity which is less than the first prescribed volume, and filling the peritoneal cavity with a tidal volume of dialysis fluid. The steps of draining the peritoneal cavity to a reserve volume and filling the peritoneal cavity with a tidal volume are then repeated for a prescribed number of cycles. At the end of (N) cycles, the method includes totally draining the dialysis fluid from the peritoneal cavity, filling the peritoneal cavity with an initial volume of dialysis fluid, draining the dialysis fluid from the peritoneal cavity until the reserve volume of dialysis fluid remains in the cavity, and filling the peritoneal cavity with a tidal volume of dialysis fluid. The draining and filling of a tidal volume are again repeated for (N) cycles. The (N) cycles are repeated until a desired amount of fluid is removed from the patient. The process includes heating the dialysis fluid prior to accumulating the dialysis fluid in the first reservoir to sterilize the dialysis fluid, and storing the dialysis fluid at a prescribed temperature and for a prescribed length of time prior to delivering the dialysis fluid to the first reservoir to kill the bacteria in the dialysis fluid.

The process includes monitoring the amount of water removed from the patient during dialysis and adjusting an amount of glucose mixed with the dialysis fluid to adjust the osmolality of the dialysis fluid and maintain a prescribed weight removal from the patient.

DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 2 is a graph illustrating a ready cycle of a sterilization process for a dialysis process according to the invention;

FIG. 2-A is a graph illustrating a regime for a peritoneal tidal dialysis process according to the invention;

FIG. 2-B is a graph illustrating a total drain cycle for a peritoneal tidal dialysis process according to the invention;

FIG. 2-C is a graph illustrating a sterilization cycle for a peritoneal dialysis process and system according to the invention;

FIG. 3 is a schematic diagram of a computer controller for a peritoneal dialysis process and system according to the invention.

DESCRIPTION OF A PREFERRED EMBODIMENT

Figure 1:
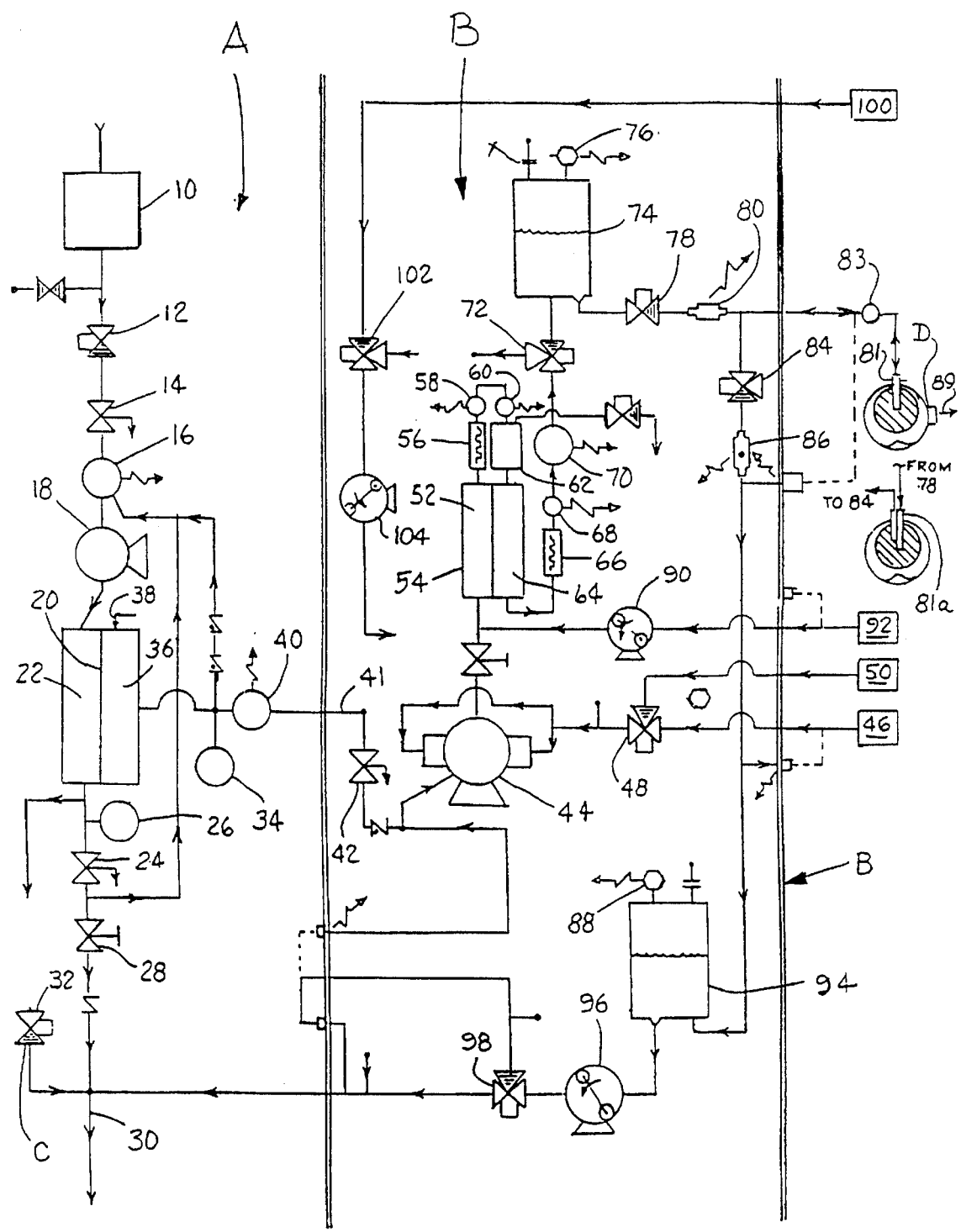
FIG. 1 is a schematic diagram of a peritoneal dialysis system and process according to the invention.

Referring now in more detail to the drawings, an illustrative embodiment of the invention will now be described. There is a reverse osmosis (RO) unit A to which water is delivered through an input filter 10 which may consist of a carbon element to remove chlorine and chloramines followed by a particle filter. A suit RO unit is manufactured by Servall Corporation of Anderson, S.C., as model 2114B. There is a main water valve 12 which is always on except in the recirculating sterilize mode. Next comes a manual pressure regulator 14 which essentially sets the product water pressure. A conductivity/temperature (C/T) probe 16 measures the incoming water conductivity and temperature and signals the electronics of RO unit A. The word "conductivity" is common in water treatment systems, and the term "TDS" as used herein stands for total dissolved solids. Pump 18 is the main RO water pump and supplies the flow and pressure to drive water across a RO membrane 20 of RO unit A. After passing through an inlet side of the RO membrane case 22 the water flow normally enters a second manual pressure regulator 24, monitored by a pressure gauge 26 which sets the membrane inlet pressure in the range of 150 to 175 psi. This is followed by a manually adjusted fluid restrictor 28 (and check valve) which adjusts the amount of water recirculating in the loop back to the connection point of probe 16. The waste water then flows down a drain 30. A valve 32 is actuated momentarily by a computer C at the beginning of a READY/RINSE cycle to allow a high flow of water through to flush inlet side 22 of membrane 20. The pressure in the output product water is monitored by a gauge 34. Note that an outlet side 36 of the membrane housing includes a formaldehyde inlet 38 where formaldehyde is introduced during a STERILIZATION. A probe 40 measures the conductivity and temperature of the product water and signals the RO electronics. The RO electronics watch both the ratio of the incoming and product water conductivity (% rejection) and the output conductivity and communicate with the computer. Both the output conductivity and the % rejections have alarm limits set by the RO electronics which signal the computer. There is a loop back from a point prior to probe 40 through two check valves which essentially diverts flow back to the connection point at probe 16 to regulate the product water pressure.

The sterile product water at 41 passes into a dialysis production unit (DPU) module B. Production unit B includes a manually set pressure regulator 42 which controls the flow rate through a check valve to a volumetric proportioning pump 44. Pump 44 precisely proportions a concentrate 46 through a valve 48 and water through 42 to make dialysate. It also proportions bleach 50 at the start of a STERILIZE/BLEACH cycle. The output of pump 44 passes through a manually set fluidic restrictor to the heat exchanger input. The proportioning pump 44 may be in the range of a 34:1 to 20:1 to allow use of available peritoneal dialysis concentrate formulations. After passing through an inlet side 52 of a heat exchanger 54, the dialysate is heated by a heater means 56, controlled by thermistor 58 and the computer, to a temperature of 70° to 80° C. and monitored by thermistor 60 and the computer. A storage means in the form of a small reservoir 62 following thermistor 60 serves two purposes, holding the fluid at that temperature for a short time to provide backup sterilization, and providing a point for air removal. In summary, heater 56 serves the dual purpose of backup sterilization and air removal. The dialysate then flows back through an opposite side 64 of heat exchanger 54 in a counterflow direction and is cooled below a heater 66 temperature set point. Heater 66 heats the dialysate to the proper patient temperature and is controlled by thermistor 68 and the computer. C/T probe 70 monitors both the temperature and conductivity of the dialysate. The computer receives the output of probe 70 and by controlling a valve 72 allows flow into a reservoir 74 only when both conductivity and temperature are within preset alarm limits. Otherwise the dialysate is diverted to drain.

The amount of fluid in reservoir 74 is precisely measured by first weighing means which includes a load cell 76 which generates a first weight signal 76a input to computer C. When the amount of fluid in reservoir 74 is correct and the cycle time is correct, the computer opens an inflow delivery means, in the form of a reservoir valve 78, to allow fluid to enter (FILL) the peritoneal cavity 81 of a patient through a flowmeter 80. Flowmeter 80 provides an inflow monitoring means which monitors a function of fluid inflow, i.e. flow rate, accumulation, etc., to measure the amount of fluid delivered into the peritoneal cavity, and generate an inflow signal 80a. The pulse output of flowmeter 80 may be totaled by computer C as a monitor or backup to the measurement by the load cell/computer system. An optional filter, such as a suitable micro pore filter, may be employed in the flow path at 83 to sterilize the dialysis fluid in the event a sterilized source is not used. After an optional dwell time (DWELL) the fluid is drained (DRAIN) by an outflow delivery means having a valve 84 opened by computer C. Note that the "A" port of valve 84 is connected to a manual sampling valve which is used to check the formaldehyde residual concentration. The drain fluid (which includes any ultrafiltrate) then passes through a flowmeter 86 which acts in a manner similar to flowmeter 80 as a backup/monitor to the fluid measurement of a load cell 88. Flowmeter 86 provides an outflow monitoring means for monitoring the outflow of fluid from the peritoneal cavity and generates an outflow signal 86a representing the amount of fluid drained which is transmitted to the computer. Flowmeters 80 and 86 may be any suitable sterilizable digital flowmeter such as an Opflowmeter manufactured by Headland Company of Racine, Wis.

Preferably, the peritoneal cavity volume is also measured by a peritoneal monitor means D, preferably either in the form of a sonic or strain band system as an additional measurement of the fluid volume in the cavity to prevent over distension. Monitor means D generates a peritoneal signal 89 which represents the volume of fluid in the peritoneal cavity at a given moment. Peritoneal signal 89 can be used by computer C to override the inflow and outflow signals, 80a and 86a, and/or the weight signals, 76a and 88a, to maintain a desired or reserve amount of fluid in the peritoneal cavity at all times.

Figure 4:
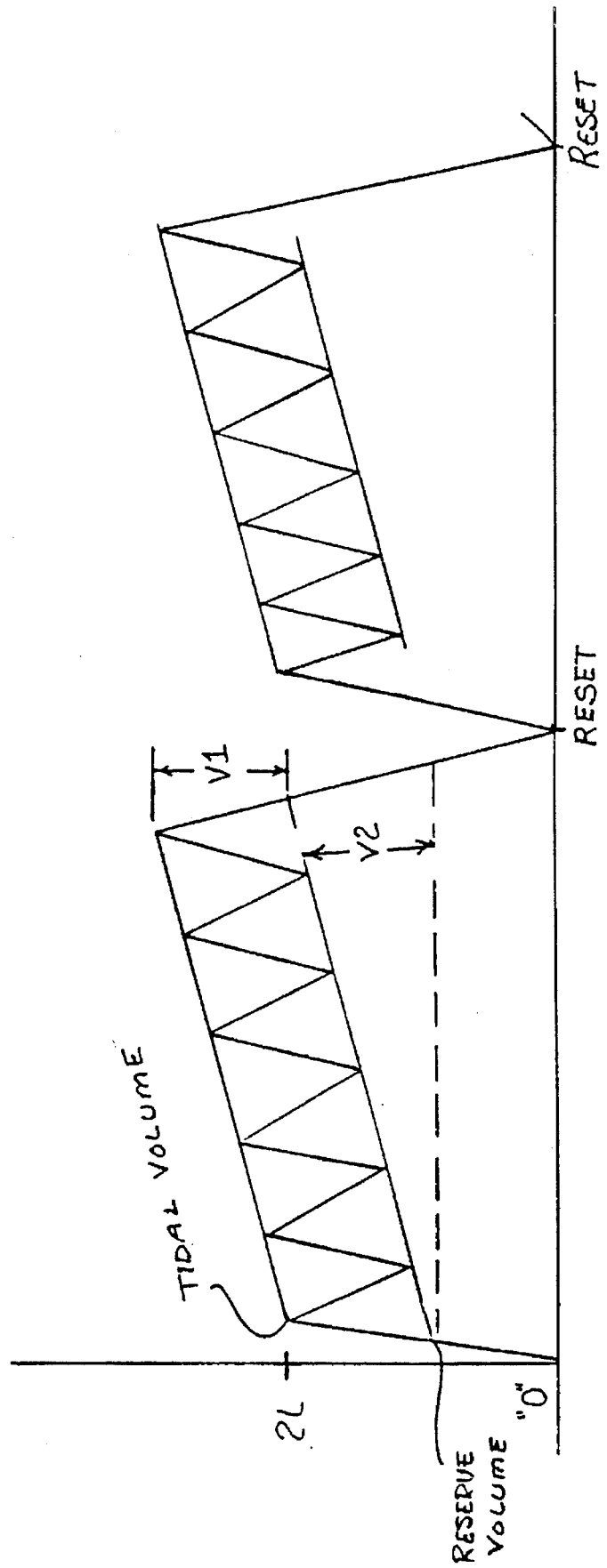
FIG. 4 is a graph of a peritoneal dialysis system and process according to the invention using a tidal dialysis regime illustrating the buildup of ultrafiltrate during the tidal process.

Sensor means for monitoring the amount of fluid removed from the patient and adjusting the osmolality of the dialysis fluid includes a dextrose pump 90 used to add dextrose 92 in addition to that contained in the peritoneal dialysis concentrate. In the tidal dialysis regime, according to the invention, a total drain occurs at the end of either a desired number (N) cycles, or time or volume of fluid which correspond to a desired number (N) of tidal fill and drain cycles. After the total drain, the total amount of water taken off the patient may be calculated by the computer and the osmolality of the solution adjusted to insure an accurate amount of ultrafiltrate is removed from the patient. As can be seen in FIG. 4, the volume of fluid in the peritoneal cavity during the tidal peritoneal dialysis process is more accurately illustrated wherein volume V1 represents the tidal drain volume and volume V2 represents the ultrafiltration volume. Thus, even though the tidal drain volume V1, which may be 1 liter, for example, is being removed, the volume of fluid in the peritoneal cavity may be increasing due to the presence of the ultrafiltration. By having a total drain of the peritoneal cavity after a desired number of drain and fill cycles, it is possible to remove the ultrafiltration and begin the dialysis process again. Referring to FIG. 4, the process begins at the origin where the peritoneal cavity volume is zero. The cavity is filled with a volume of 2 liters and then drained with a volume of 1 liter, as shown in the example of FIG. 4. Because there may be some ultrafiltrate, the draining of 1 liter will not necessarily result in a reserve volume of 1 liter. The ultrafiltrate will increase this volume as shown at V2. In accordance with the invention, at the reset point there is a total drain, the amount of ultrafiltrate is measured, and the remaining weight to be removed from the patient is calculated. If the dialysis process is not removing weight at a sufficient rate, the osmolality of the dialysis solution may be adjusted by increasing the dextrose amount so that more weight is removed from the patient during the next dialysis regime consisting of tidal fill and drain cycles. If too much weight has been removed during the previous dialysis regime, then the dextrose can be decreased. At the beginning of the dialysis process, the dry weight of the patient has been calculated along with the specific amount of weight desired to be removed from the patient. It may be desirable to increase the maximum flow rate of pump 90 from 10 m./min (2%) to 15 m./min (3%) since concentrate dextrose amounts over 1.8% (diluted) tend to be unstable. The actual ultrafiltrate may be measured by calculating the amount of patient fluid removal, and pump 90 automatically adjusted to obtain the desired ultrafiltration amount. There is no backup monitor on pump 90. This may be considered a non-critical condition or might be monitored roughly by probe 70 since the dextrose decreases the conductivity.

The drain fluid enters a drain reservoir 94 where the amount is precisely monitored by a second weighing means which includes a load cell 88 which generates a second weight signal 88a input to the computer. The second weight signal represents an amount that includes both the fill volume and the ultrafiltrate and is stored by the computer. Note that the readings and signals obtained from weighing means 76 and 88, and flow monitoring means 80 and 86, are also used to monitor that proper flow is going into and out of the patient, that is there is no flow blockage such as would occur with a kinked line. Hydrophobic filters at the tops of 74 and 94 allow sterile air in and out of the reservoirs but block fluid flow. Drain pump 96 drains reservoir 94 during the fill and dwell cycles.

Pump 96 also acts as the recirculating pump during the STERILIZE/RECIRCULATION part of the cycle. A valve 98 is a redundant (safety) element to the drain pump 96 and is also used to switch the drain flow in the STERILIZE/RECIRCULATING mode. The manual switching of the "A" output of valve 98 serves as a redundant (safety) element. The drain fluid then goes down drain 30.

In the READY cycle, as can best be seen in FIG. 2, the system is first rinsed out for at least 20 minutes to remove the formaldehyde and then pause for a test. If the test is negative, the patient then moves the concentrate, dextrose, and output lines of pump 98 to their RUN modes (safety) and proceed on into WARMUP if the computer reads that all the interlock switches are in their proper condition. The system then prepares the dialysate and fills reservoir 74 where we again go into a hold cycle while the patient is connected. The "install set" and "prime" portions of the cycle are no longer used. Then the RUN cycle is begun.

As can best be seen in FIG. 2A, the peritoneal cavity is initially drained of any excess fluid and then filled to two liters (for example) and then the FILL/DRAIN or the FILL/DWELL/DRAIN portion of the cycle is started. Every $N^{th}$ cycle, preferably N=10, the peritoneal cavity is totally drained and the actual amount is compared to that predicted. The computer then resets the fill and drain parameters to correct any significant deviation. Note that this is the method used to maintain a tidal volume in the patient, which is the difficult part of tidal peritoneal dialysis. Also, the actual ultrafiltrate is measured by weighing means 76 and 88 and the computer, and this predictive parameter is reset. At the end of the RUN cycle, the patient is completely drained.

In the STERILIZE cycle, as can best be seen in FIG. 2C, the system is first cleaned with bleach for 20 minutes, the bleach rinsed out, and then the system is filled with formaldehyde, around 8% in the RO and 4% in the main flow lines and path. Then there is a switch to a recirculating mode wherein the 4% formaldehyde is circulated at 37° C. or higher for six hours. The conductivity of the bleach is monitored which has a naturally conductivity of around 7.5 ms/cm at a 0.25% concentration, and the concentration of the formaldehyde which has had sodium chloride added to give a conductivity of 4.0 ms/cm at 4%. Both conductivities are monitored by the computer, along with the temperature (both signals coming from 70) which would alarm if the proper signal were not received for the proper time. The system then shuts totally down to wait for the READY cycle to be initiated.

In accordance with the method of the invention, there is first a READY/RINSE cycle in order to prepare the system for the patient. During the READY/RINSE cycle, the formaldehyde is reduced to 5 ppm at the patient line. Formaldehyde from source 100 passes through valve 102 and is pumped by pump 104 to the RO membrane 20 through inlet 38. The system is drained and then flushed with RO water at 500 ml/min., alternating certain valves to catch all of the lines. The system is then held to allow time for testing for residual formaldehyde, and then the dialysis concentrate is hooked up and shifted to several other lines. The system is then warmed up with sterile, mixed, heated dialysate ready for patient connection. The continuous peritoneal dialysis process, during the patient cycle, includes the steps of initially draining the patient's peritoneal cavity of any residual fluid. Next, the patient cycle includes a fill cycle and a drain cycle. Optionally, there may be a dwell cycle between the fill and drain cycles. In the preferred embodiment, the fill and drain cycles are repeated a prescribed number of times. Afterwards, there is a total drain of the peritoneal and the total fluid in and out of the peritoneal are calculated by the computer. The system parameters are reset according to the calculations of fluid in and out for efficient dialysis, i.e. the glucose is adjusted to desired osmolality. The amount of fluid entering and leaving the patient is measured by the precision load cells on the reservoirs, backed up by the input and output flowmeters, and optionally backed up by the peritoneal volume measurement.

In operation, when the prescribed weight or volume of dialysis fluid is sensed by load cell 76, the valve 72 is closed. When valve 78 is opened, the heated sterilized dialysate flows through valve 78 and flowmeter 80 to the catheter 81 in the peritoneal cavity C of the patient. Valve 78 is closed as soon as a prescribed weight (i.e. volume, etc.) of the dialysate is delivered from reservoir 74. Reservoir 74 is not depleted in the run mode. It outflows to a predetermined level established by the computer. Reservoir 74 is depleted during rinse and warm-up stages. When a prescribed weight of fluid has been drained from reservoir 94, as measured by load cell 88, and valve 84 is closed and calculated by computer C. The drain cycle commences by the opening of valve 84 and fluid from the peritoneal cavity flows through valve 84 and flowmeter 86 to reservoir 94. When the system is to be reset and for the final drain, load cell 88 senses no weight change for a predetermined length of time, i.e. end of fluid draining, and the drain cycle is terminated by the closing of valve 84. The computer receives a input representing the predetermined level at 88 to control tidal volume. During the drain cycle, head vessel 74 is replenished with heated sterilized dialysate. The fill and drain cycles are then repeated. Optionally, there may be a dwell time between the end of the fill cycle and the beginning of the drain cycle. In the tidal technique, the tidal volume is assumed to be 50% of the fill volume in the preferred embodiment, but may vary in accord with the application. In the tidal peritoneal dialysis technique, there is an initial fill cycle in which the peritoneal is initially filled to a first limit, for example, 2 liters. The initial drain cycle drains the peritoneal to a reserve volume greater than zero. For example, the drain cycle may drain the patient from 2 liters to a reserve volume of 1 liter so that 1 liter remains in the patient, as can best be seen in FIG. 2A. In subsequent fill and drain cycles, a tidal volume of approximately 1 liter is infused into the cavity and approximately 1 liter is drained from the cavity. In this sense, the system and method of the present invention provide an automatic tidal dialysis system. At the end of the fill/drain cycles, a complete drain of the patient occurs. The system is reset by calculating the patient weight removal, adjusting the osmolality of the dialysis fluid and again initially filling the peritoneal cavity with a prescribed amount of dialysis fluid. Other variations of this procedure may be had. The object is to achieve effective sterilization in a short time with minimal rinse out problems. The control means may be any suitable computer C such as a conventional process controller programmed to automatically compute and carry out the above described functions and control the various hardware elements illustrated in FIG. 3. The peritoneal dialysis system of the invention may be used with either a single catheter 81 or a double peritoneal catheter 81a. In the case of a double catheter 81a, the inflow and outflow delivery means, 78 and 84, may be controlled by the control means so that dialysis fluid flows in and out simultaneously or alternately. While the use of inflow and outflow measuring means 80 and 86 are preferred when the double catheter is used, weighing means 76 and 88 are optional and may not be employed. Dialysis fluid may be delivered directly to the peritoneal cavity, and reservoirs 74 and 94 may be eliminated. Furthermore, flow measuring means may also be optional when using weighing means 76, 88 and reservoirs 74, 94 in the application of a single catheter. In RO unit A, the input conductivity and temperature from probe 16 and the output conductivity and temperature from probe 40 may be used to provide an alarm indicating failure in the membrane integrity if either the percent rejection or the output quality differ from set limits. In production unit D, the volumes in reservoirs 74 and 94 are measured by load cells 76 and 88. The inflow and outflow rates to the patient will be monitored either by a combination of the load cell readings and time, or flowmeters 80 and 86. In addition, either an ultrasonic or strain gauge band may be utilized to indicate the approximate peritoneal cavity volume. Probe 70 will output the conductivity and temperature of dialysate to reservoir 74 which may be diverted if the conductivity and temperature exceed plus or minus 1 ms/cm or 3° C.

While a preferred embodiment of the invention has been described using specific terms, such description is for illustrative purposes only, and it is to be understood that changes and variations may be made without departing from the spirit or scope of the following claims.

What is claimed is:

1. A system for performing a continuous peritoneal dialysis process which includes a fill cycle and a drain cycle during which body waste fluid is removed, said system comprising:

continuous source of sterilized dialysis fluid which contains an osmotic substance;

an inflow line connected to said source of dialysis fluid for delivering said dialysis fluid from said source to a peritoneal cavity of a patient during the fill cycle, and an inflow delivery means disposed in said inflow line for controlling the inflow of said dialysis fluid;

an outflow line adapted to be operatively connected to the peritoneal cavity for draining dialysis fluid from the peritoneal cavity of the patient during the drain cycle, and an outflow delivery means disposed in said outflow line for controlling the outflow of said dialysis fluid;

means in communication with said inflow line for measuring an inflow of said dialysis fluid through said inflow line and generating an inflow signal;

means in communication with said outflow line for measuring an outflow of said dialysis fluid through said outflow line and generating an outflow signal;

control means communicating with said delivery means for receiving said inflow and outflow signals for controlling said inflow and outflow delivery means in response to said inflow and outflow signals to control the amount of said inflow and outflow of dialysis fluid; and sensor means communicating with said outflow line determining the amount of the body waste fluid removed from the peritoneal cavity during said inflow and outflow of said dialysis fluid, and proportioning means operatively associated with said sensor means for adjusting the amount of said osmotic substance contained in said dialysis fluid during subsequent fill and drain cycles in order to remove a desired body weight.

2. The system of claim 1 including monitor means for monitoring a function of a fluid volume contained within the peritoneal cavity, and said control means operatively connected to said monitor means to control said inflow or outflow delivery means in response to said monitoring means to maintain a desired fluid volume in the peritoneal cavity.

3. The system of claim 2 wherein said monitor means includes an ultrasonic sensing means.

4. The system of claim 2 wherein said monitor means includes a resistive sensing means.

5. The system of claim 1 wherein said control means controls said inflow and outflow delivery means so as to maintain a desired reserve volume of dialysis fluid remaining in the peritoneal cavity during the fill and drain cycles which is effective for dialysis.

6. The system of claim 1 wherein:

said control means controls said inflow and outflow delivery means for initially filling said peritoneal cavity with a tidal volume of dialysis fluid, partially draining said dialysis fluid from said peritoneal cavity to leave a reserve volume of dialysis fluid remaining in said cavity after the drain cycle which is less than said tidal volume, and refilling the peritoneal cavity with said tidal volume of dialysis fluid; and said control means controls said inflow and outflow delivery means to repeat filling of the peritoneal cavity with said tidal volume and partial draining of the peritoneal cavity to said reserve volume for providing a prescribed dialysis regime which includes a desired number (N) of the filling and draining cycles.

7. The system of claim 6 wherein said control means:

controls said outflow delivery means for totally draining said dialysis fluid from the peritoneal cavity at the end of said (N) cycles; and controls said inflow and outflow delivery means to repeat a number of said dialysis regimes until a desired amount of the waste fluid is removed from the patient.

8. The system of claim 7 wherein said sensor means senses and calculates the amount of the waste fluid removed from the patient after totally draining said dialysis fluid, and said proportioning means adjusts an amount of said osmotic substance mixed with said dialysis fluid in response to said sensor means for subsequent cycles.

9. The system of claim 1 including heater means operatively associated with said dialysis fluid for heating said dialysis fluid prior to delivery of said dialysis fluid through said inflow line to sterilize said dialysis fluid.

10. The system of claim 1 including measuring means operatively associated with said dialysis fluid for measuring the conductivity of said dialysis fluid prior to delivering said dialysis fluid.

11. The system of claim 1 wherein said control means controls said inflow and said outflow delivery means to maintain said dialysis fluid within said peritoneal cavity for a prescribed dwell time between the filling and draining cycles.

12. A system for performing a continuous peritoneal dialysis process which includes a fill cycle and a drain cycle during which body waste fluid is removed, said system comprising:

a continuous supply system which includes a source of purified water, a source of concentrated dialysate, and a source of an osmotic substance which may be mixed for providing a continuous supply of sterilized dialysis fluid;

inflow delivery means associated with said supply system for filling a peritoneal cavity of a patient with said dialysis fluid from said supply system during the fill cycle;

outflow delivery means for being operatively connected with the peritoneal cavity for draining said dialysis fluid from the peritoneal cavity during the drain cycle;

inflow measuring means operatively connected in said system for measuring and monitoring a function of an inflow of dialysis fluid which fills the peritoneal cavity and generating an inflow signal representing the amount of fluid delivered into the peritoneal cavity;

outflow measuring means operatively connected in said system for measuring and monitoring a function of an outflow of dialysis fluid and generating an outflow signal representing the amount of fluid drained from the peritoneal cavity;

control means receiving said inflow and outflow signals for controlling said inflow delivery means to control the amount of dialysis fluid delivered to the peritoneal cavity, and for controlling said outflow delivery means to control the amount of dialysis fluid drained from the peritoneal cavity to maintain a desired amount of dialysis fluid in the patient during dialysis in response to said inflow and outflow signals; and sensor means operatively connected in said system for monitoring the amount of body waste fluid removed from the patient during draining said dialysis fluid and proportioning means operatively associated with said sensor means for adjusting an amount of said osmotic substance in said dialysis fluid in response to said sensor means to adjust the osmolality and accurately remove a prescribed weight of ultrafiltrate from the patient during subsequent fill and drain cycles.

13. The system of claim 12 including a double flow catheter for implantation into the peritoneal cavity of said patient, and said double flow catheter having an inflow and outflow passage connected to said inflow and outflow delivery means, respectively, for simultaneously delivering dialysis fluid into and out of the peritoneal cavity.

14. The system of claim 13 wherein said control means controls said inflow and outflow delivery means so that inflow and outflow occur in said inflow and outflow passages simultaneously.

15. The system of claim 13 including monitor means for monitoring a function of a fluid volume of fluid contained within the peritoneal cavity, and said control means operatively connected to said monitor means to control said inflow or outflow delivery means in response to said monitoring means to maintain a desired fluid volume in the peritoneal cavity.

16. The system of claim 12 including monitor means for monitoring said fluid volume in the peritoneal cavity and generating a peritoneal signal representing the fluid volume of the peritoneal cavity, and said control means operatively connected to said monitor means to adjust said inflow and outflow delivery means in response to said peritoneal signal whereby said control means maintains a desired fluid volume in the peritoneal cavity.

17. The system of claim 16 wherein said monitor means includes an ultrasonic sensing means.

18. The system of claim 16 wherein said monitor means includes a resistive sensing means.

19. The system of claim 12 wherein said control means controls said inflow and said outflow delivery means for filling and draining said dialysis fluid between a tidal fill volume and a reserve drain volume to maintain a desired volume of dialysis fluid in the peritoneal cavity during dialysis which is effective for dialysis.

20. The system of claim 12 wherein:

said control means controls said inflow and outflow delivery means for initially filling the peritoneal cavity with a tidal volume of dialysis fluid, partially draining said dialysis fluid from the peritoneal cavity to leave a reserve volume of dialysis fluid in the cavity which is less than said tidal volume, and refilling the peritoneal cavity with said tidal volume of dialysis fluid; and said control means controls said inflow and outflow delivery means to repeat filling of the peritoneal cavity with said tidal volume and partial draining of the peritoneal cavity to said reserve volume for providing a prescribed dialysis regime which includes a desired number (N) of the filling and draining cycles.

21. The system of claim 20 wherein said control means:

controls said outflow delivery means for totally draining said dialysis fluid from the peritoneal cavity at the end of said (N) cycles; and controls said inflow and outflow delivery means to repeat a number of said dialysis regimes until a desired amount of body waste is removed from the patient.

22. The system of claim 12 including heater means operatively connected to said source of dialysis fluid for heating said supply of sterilized dialysis fluid to sterilize said dialysis fluid.

23. The system of claim 22 including storage means in fluid communication with said heater means for storing said heated supply of sterilized dialysis fluid at a prescribed temperature and for a prescribed length of time prior to delivering said dialysis fluid to the peritoneal cavity to kill the bacteria in said dialysis fluid.

24. The system of claim 12 wherein said control means controls said inflow delivery means and said outflow delivery means to maintain said dialysis fluid within said peritoneal cavity for a prescribed dwell time between said filling and draining.

25. A system for performing a continuous peritoneal dialysis process comprising:

accumulation means including a first reservoir in which a sterilized dialysis fluid is accumulated;

inflow delivery means connected to said first reservoir for delivering said dialysis fluid from said first reservoir to a peritoneal cavity of a patient;

means for determining the amount of said dialysis fluid delivered to the peritoneal cavity and generating a first signal;

outflow delivery means for draining dialysis fluid from the peritoneal cavity of the patient;

means for determining the amount of said dialysis fluid drained from the peritoneal cavity and generating a second signal;

control means receiving said first and second signals for controlling said inflow delivery means and filling of the peritoneal cavity in response to said first signal, and for controlling said outflow delivery means and draining of said dialysis fluid from the peritoneal cavity in response to said second signal;

said control means controlling said inflow delivery means for initially filling the peritoneal cavity with an initial tidal, fill volume of dialysis fluid;

said control means controlling said outflow delivery means after establishing said initial fill volume for partially draining a preset drain volume of said dialysis fluid from the peritoneal cavity during a drain cycle to leave a reserve volume of dialysis fluid in the peritoneal cavity which is less than said initial fill volume yet is effective for dialysis;

said control means controlling said inflow means after the drain cycle for refilling the peritoneal cavity with a preset fill volume of dialysis fluid during a fill cycle;

said control means repeatedly controlling said inflow and outflow delivery means in alternating drain and fill cycles to create a tidal pool of dialysis which fluctuates in volume according to said fill and drain volumes;

said control means controlling said inflow and outflow delivery means to repeat the drain and fill cycles a desired number (N) of cycles defining a complete tidal dialysis regime; and said control means also controlling said outflow delivery means to totally drain said dialysis fluid from the peritoneal cavity at the end of said tidal dialysis regime to remove the ultrafiltrate from the patient.

26. The system of claim 25 wherein said control means: controls said inflow and outflow delivery means to repeat a number of said tidal dialysis regimes until a desired amount of water is removed from said patient.

27. The system of claim 26 including a dialysis fluid which includes an osmotic substance, and including sensor means operatively connected to the system for monitoring the amount of water removed from the patient during dialysis after said total drain of each tidal dialysis regimes and a proportioning means operatively connected to said sensor means for adjusting an amount of said osmotic substance in said dialysis fluid to adjust the osmolality and accurately remove a prescribed weight from the patient during subsequent fill and drain cycles.

28. The system of claim 25 wherein said preset fill volume and preset drain volume are generally equal.

* * * * *